(12) United States Patent
Yao et al.

(10) Patent No.: US 12,037,632 B2
(45) Date of Patent: Jul. 16, 2024

(54) RECOMBINANT EXPRESSION VECTOR APPLICABLE TO RAPID SCREENING FOR RECOMBINANT STRAIN AND APPLICATION

(71) Applicant: FEED RESEARCH INSTITUTE, CHINESE ACADEMY OF AGRICULTURAL SCIENCES, Beijing (CN)

(72) Inventors: Bin Yao, Beijing (CN); Xiaoyun Su, Beijing (CN); Fei Gao, Beijing (CN); Huiying Luo, Beijing (CN); Huoqing Huang, Beijing (CN); Yingguo Bai, Beijing (CN); Yuan Wang, Beijing (CN); Tao Tu, Beijing (CN); Yaru Wang, Beijing (CN); Kun Meng, Beijing (CN)

( * ) Notice: Subject to any disclaimer, the term of this patent is extended or adjusted under 35 U.S.C. 154(b) by 535 days.

(21) Appl. No.: 17/263,562

(22) PCT Filed: Jul. 13, 2019

(86) PCT No.: PCT/CN2019/095900
§ 371 (c)(1),
(2) Date: Jan. 27, 2021

(87) PCT Pub. No.: WO2020/020003
PCT Pub. Date: Jan. 30, 2020

(65) Prior Publication Data
US 2021/0388411 A1    Dec. 16, 2021

(30) Foreign Application Priority Data
Jul. 27, 2018   (CN) .......................... 201810841004.0

(51) Int. Cl.
| | | |
|---|---|---|
| *C12Q 1/40* | (2006.01) | |
| *C07K 14/38* | (2006.01) | |
| *C07K 14/435* | (2006.01) | |
| *C12N 15/80* | (2006.01) | |
| *G01N 15/14* | (2024.01) | |
| *C12R 1/885* | (2006.01) | |

(52) U.S. Cl.
CPC ............... *C12Q 1/40* (2013.01); *C07K 14/38* (2013.01); *C07K 14/43504* (2013.01); *C12N 15/80* (2013.01); *G01N 15/1468* (2013.01); *C07K 2319/035* (2013.01); *C07K 2319/60* (2013.01); *C12R 2001/885* (2021.05); *G01N 2015/1472* (2013.01); *G01N 2333/93* (2013.01)

(58) Field of Classification Search
CPC ....................................................... C12Q 1/40
See application file for complete search history.

(56) References Cited

FOREIGN PATENT DOCUMENTS

| | | |
|---|---|---|
| CN | 101759784 A | 6/2010 |
| CN | 102268448 A | 12/2011 |
| CN | 102876706 A | 1/2013 |

OTHER PUBLICATIONS

ISR; China National Intellectual Property Administration; Nov. 22, 2019.
Gao; Fei et al; "A Versatile System for Fast Screening and Isolation of Trichoderma Reesei Cellulase Hyperproducesrs Based on DSRED and Fluorescence-Assisted Cell Sorting" Biotechnology for Biofuels, vol. 26, No. 11, Sep. 24, 2018.
Su, Jianchen et al; "Construction of a Cell-Surface Expression System in Trichoderma Reesei; Acta Microbiologica Sinica"; Jan. 4, 2013.
LV, Dandan et al; "Construction of Two Vectors for Gene Expressionin Trichoderma Reesei"; Plasmid, vol. 67, No. 1; Jan. 31, 2012.
Liu, Gang et al; "Expression of the Red Fluorescent Protein in the Filamentous Fungus Trichoderma Reesei"; Biotechnology, vol. 16, No. 6—Dec. 31, 2006.
Liu, Gang et al; "Analysis of Cellulase Synthesis Mechanism in Trichoderma Reesei Using Red Fluorescent Protein"; Acta Microbiologica Sinica; vol. 47, No. 1; Feb. 4, 2007.

*Primary Examiner* — Suzanne M Noakes
(74) *Attorney, Agent, or Firm* — Patshegen IP; Moshe Pinchas

(57) ABSTRACT

The present invention relates to the field of genetic engineering, particularly to a recombinant expression vector for rapidly screening the high expression strains and a method for rapidly screening high expression strains. In the invention, an exogenous red fluorescent protein and *Aspergillus fumigatus* cell surface protein localization signal are fused and expressed, and the fusion gene (DsRed-AfMP1) is integrated into the genome of *Trichoderma reesei*, so as to construct a strain displaying red fluorescent protein on the surface of *Trichoderma reesei*. By sorting *Trichoderma reesei* strains with red fluorescent protein on the surface by flow cytometry, genes beneficial to the improvement of cellulase activity can be quickly isolated.

4 Claims, 4 Drawing Sheets
Specification includes a Sequence Listing.

RECOMBINANT EXPRESSION VECTOR APPLICABLE TO RAPID SCREENING FOR RECOMBINANT STRAIN AND APPLICATION

SEQUENCE LISTING

The contents of the electronic sequence listing created on (07-02-2021), named 20120-amended sequence listing.txt and 16,546 bytes in size, is hereby incorporated by reference in its entirety.

FIELD OF THE INVENTION

The present invention relates to the field of genetic engineering, particularly to a recombinant expression vector for rapid screening recombinant strains and application thereof.

BACKGROUND OF THE INVENTION

Plant cell wall is mainly composed of cellulose, hemicellulose and lignin, wherein cellulose as the main component of cell wall, is a kind of natural linear macromolecular polymer formed by 8000-10000 glucose linked by β-1,4-glycosidic bond, having the basic unit of cellobiose. Complex cellulase enzyme systems are required to degrade cellulose polysaccharides of plant cell walls into fermentable simple oligosaccharides and monosaccharides such as glucose.

*Trichoderma reesei*, as one of the main filamentous fungi, has a strong ability of secreting cellulase, which can be modified to industrially produce more than 100 g/L of cellulase yield. Therefore, it has important application value in degradation of plant cell wall polysaccharides and related applications thereof.

The cellulase system of *Trichoderma reesei* includes two exocellulases, five endocellulases, one β-glucosidase and three lytic polysaccharides monooxygenases (LPMOs, i.e. the former member of GH61 family).

With the continuous optimization of the genetic operation system of *Trichoderma reesei*, the transformation efficiency has basically met the industrial needs but, it brings a new key problem how to screen those efficiently expressing the target protein when a large number of transformants are obtained. *Trichoderma reesei* is a filamentous fungus with a multinucleate colony of the multinucleated hyphae that intertwine to form mycelial pellets, which is different from the common pure strain colonies. In order to obtain the transformants line on the transformation plate against high false-positive background, it is necessary to isolate mononuclear spores with the tedious single spore isolation process, which leads to a long genetic modification cycle, and taking more time and laborious to screen high expression strains.

Flow cytometry is a technique for rapid quantitative analysis and sorting of the single cell or the other biological particles in liquid flow, which can analyze tens of thousands of cells at a high speed, while measuring the multiple cell characteristic parameters of one cell for qualitative or quantitative analysis, and therefore is characteristics of high speed, high precision and good accuracy. However, the prior flow cytometry can only detect the changes of the regulatory factors acting during the transcription stage, but unable to detect the changes of regulatory factors after transcription. *Trichoderma reesei* cellulase is secreted and expressed after transcription, translation, transport and glycosylation, rather than intracellular expression. Therefore, the prior flow cytometry only able to detect the change of transcription level, which can't meet the requirements of screening cellulase with improved enzyme activity.

ORDER OF THE INVENTION

In order to solve the problem that the prior technology can not quickly screen the *Trichoderma reesei* transformants with improved enzyme activity, the present invention provides a recombinant expression vector for rapid screening of recombinant strains and application thereof. The invention can quickly screen *Trichoderma reesei* strains highy producing cellulase, greatly shorten the screening time, improve the screening efficiency, and obtain high-yield pure line transformants to meet the needs of practical production.

The order of the present invention is to provide a recombinant expression vector for rapidly screening high expression strains.

Another order of the present invention is to provide a recombinant strain containing the above recombinant expression vector.

Another order of the present invention is to provide a method for rapidly screening *Trichoderma reesei* highly expressing cellulase.

Another order of the present invention is to provide a method for rapidly screening *Trichoderma reesei* highly expressing cellulase with high enzyme activity.

In a preferred embodiment of the present invention, a recombinant expression vector for rapidly screening high expression strains including a gene expression cassette comprising elements of cbh1 promoter, red fluorescent protein gene DsRed, cell surface protein anchor signal peptide gene AfMp1 and cbh1 terminator in order from upstream to downstream, wherein the said gene DsRed has the nucleotide sequence showing in SEQ ID No: 2, the said gene AfMp1 has the nucleotide sequence showing in SEQ ID No: 3, and the nucleotide sequence of cbh1 promoter is shown in SEQ ID No: 1.

SEQ ID No: 1

Tcaacctttggcgtttccctgattcagcgtacccgtacaagtcgtaatc actattaacccagactgaccggacgtgttttgcccttcatttggagaaa taatgtcattgcgatgtgtaatttgcctgcttgaccgactgggctgtt cgaagcccgaatgtaggattgttatccgaactctgctcgtagaggcatg ttgtgaatctgtgtcgggcaggacacgcctcgaaggttcacggcaaggg aaaccaccgatagcagtgtctagtagcaacctgtaaagccgcaatgcag catcactggaaaatacaaaccaatggctaaaagtacataagttaatgcc taaagaagtcatataccagcggctaataattgtacaatcaagtggctaa acgtaccgtaatttgccaacggcttgtggggttgcagaagcaacggcaa agccccacttccccacgtttgtttcttcactcagtccaatctcagctgg tgatcccccaattgggtcgcttgtttgttccggtgaagtgaaagaagac agaggtaagaatgtctgactcggagcgttttgcatacaaccaagggcag tgatggaagacagtgaaatgttgacattcaaggagtatttagccaggga tgcttgagtgtatcgtgtaaggaggtttgtctgccgatacgacgaatac tgtatagtcacttctgatgaagtggtccatattgaaatgtaagtcggca ctgaacaggcaaaagattgagttgaaactgcctaagatctcgggccctc -continued

```
gggccttcggcctttgggtgtacatgtttgtgctccgggcaaatgcaaa gtgtggtaggatcgaacacactgctgcctttaccaagcagctgagggta tgtgataggcaaatgttcaggggccactgcatggtttcgaatagaaaga gaagcttagccaagaacaatagccgataaagatagcctcattaaacgga atgagctagtaggcaaagtcagcgaatgtgtatatataaaggttcgagg tccgtgcctccctcatgctctccccatctactcatcaactcagatcctc caggagacttgtacaccatcttttgaggcacagaaacccaatagtcaac cgcggactgcgcatcatgtatcggaagttggccgtcatctcggccttct tggccacagctcgtgct
```

The nucleotide sequence of DsRed gene is shown in SEQ ID No: 2.

SEQ ID No: 2
```
ggcggctccggctccggctccggctccagcactggtactgccactgcct ccaccagcaccaacctcctcAAGactggcgccgccagcaaggagcactt cagctactccctcggcggtgccgtcgtcgcggccgccatcgccgtcgct ctctaa
```

The nucleotide sequence of AfMp1 gene is shown in SEQ ID No: 3.

SEQ ID No: 3
```
Atggacaacaccgaggacgtcatcaaggagttcatgcagttcaaggtgc gcatggagggctccgtgaacggccactacttcgagatcgagggcgaggg cgagggcaagccctacgagggcacccagaccgccaagctgcaggtgacc aagggcggcccctgcccttcgcctgggacatcctgtccccccagttcc agtacggctccaaggcctacgtgaagcaccccgccgacatccccgacta catgaagctgtccttccccgagggcttcacctgggagcgctccatgaac ttcgaggacggcggcgtggtggaggtgcagcaggactcctccctgcagg acggcaccttcatctacaaggtgaagttcaagggcgtgaacttccccgc cgacggccccgtaatgcagaagaagactgccggctgggagccctccacc gagaagctgtaccccagcagacggcgtgctgaagggcgagatctcccacg ccctgaagctgaaggacggcggccactacacctgcgacttcaagaccgt gtacaaggccaagaagcccgtgcagctgcccggcaaccactacgtggac tccaagctggacatcaccaaccacaacgaggactacaccgtggtgggc agtacgagcacgccgaggcccgccactccggctcccag
```

The nucleotide sequence of cbh1 terminator is shown in SEQ ID No: 4

SEQ ID No: 4
```
Agctccgtggcgaaagcctgacgcaccggtagattcttggtgagcccgt atcatgacggcggcgggagctacatggccccgggtgatttatttttttt gtatctacttctgaccctttcaaatatacggtcaactcatctttcact ggagatgcggcctgcttggtattgcgatgttgtcagcttggcaaattgt ggattcgaaaacacaaaacgattccttagtagccatgcattttaagata acggaatagaagaagaggaaattaaaaaaaaaaaaaaacaaacatcc cgttcataaccgtagaatcgccgctcttcgtgtatcccagtaccacgg caaaggtatttcatgatcgttcaatgagatattgacccgccagtatggc tccaccccatctccgcgaatctcctcactcgaacgcggtagtggcgcg ccaattggtaatgacccataggggagacaaacagcataatagcaacagtg gaaatt
```

The present invention also provides a recombinant strain comprising the said recombinant expression vector, and the recombinant strain is preferably *Trichoderma reesei*.

The present invention also provides a method for rapid screening recombinant *Trichoderma reesei* including the steps of (1) introducing the gene expression cassette containing cbh1 promoter, red fluorescent protein gene DsRed, cell surface protein anchor signal peptide gene AfMp1 and cbh1 terminator into the plasmid to obtain the recombinant expression vector, wherein the said gene DsRed has the nucleotide sequence of SEQ ID No: 2, and the said gene AfMp1 has the nucleotide sequence of SEQ ID No: 3;

(2) transforming the host cell with the recombinant vector constructed in step (1) to obtain the recombinant strain;

(3) cultivating the recombinant strain and inducing to express the red fluorescent protein on the surface of the said recombinant strain; and (4) screening of the recombinant strains showing red fluorescence.

In a yet preferred embodiment of the present invention, the recombinant strains showing red fluorescence on the surface are screened by flow cytometry.

The present invention also provides a method for the rapidly screening *Trichoderma reesei* highly expressing cellulase with high enzyme activity including the steps of:

(1) introducing the gene expression cassette containing the elements of cbh1 promoter, red fluorescent protein gene DsRed, cell surface protein anchor signal peptide gene AfMp1 and cbh1 terminator into the plasmid to obtain the recombinant expression vector, wherein the said gene DsRed has the nucleotide sequence of SEQ ID No: 2, and the said AfMp1 gene has the nucleotide sequence of SEQ ID No: 3;

(2) transforming the host cell with the said recombinant vector constructed in step (1) to obtain the recombinant *Trichoderma reesei*;

(3) introducing the gene related to protein secretion pathway into the said recombinant *Trichoderma reesei* obtained in step (2), or inserting vectors or genes randomly into the recombinant *Trichoderma reesei* obtained in step (2) to obtain the mutant library of recombinant *Trichoderma reesei*;

(4) screening of the recombinant *Trichoderma reesei* strongly showing the red fluorescence on its surface by flow cytometry; and (5) determining the cellulase activity of the recombinant *Trichoderma reesei* obtained in step (4) to obtain the recombinant *Trichoderma reesei* with improved cellulase activity.

In a yet preferred embodiment of the present invention, the method according to the present invention, in step (3), the said genes related to protein secretion pathway include bip1 gene, hac1 gene, ftt1 gene, sso2 gene, sar1 gene, or ypt1 gene, wherein the nucleotide sequence of bip1 gene is shown in SEQ ID No: 5, and the nucleotide sequence of hac1 gene is shown in SEQ ID No: 6.

SEQ ID No: 5 ataaagtggcccatcgtcacctctcggcttcaactcgagttttccctt
tttccttttcttcttcttcttcaaacaaagataccccccctcaacccgg
tgcaaccagcctggtccgaggacaaaacacgatagagctcgctgcgttg
gatcgctgcgcgtcttctcttgttctctctctcttttcttctctgcaac
gcttataactcttttgcgcggggcatctgggaaaaccgtttcttcaca
catctcttcttccacaatggctcgttcacggagctccctggccctcggg
ctgggcctgctctgctggatcacgctgctcttcgctcctctggcgtttg
tcggaaaggccaatgccgcgagcgacgacgcggacaactacggcactgt
tatcggaattgtaagtcgactgacggcagcaaccccgccattttcttgg
tgttgatgctcaggcagccctgctaacacgcttctcctccgcccaggat
ctcggaactacctacagctgcgtcggtgtgatgcagaagggcaaggttg
agattctcgtcaacgaccaggtaaccgaatcactccctcctacgtggc
ctttaccgacgaggagcgtctggttggcgattccgccaagaaccaggcc
gccgccaaccccaccaacaccgtctacgatgtcaagtcagttctaccgc
cctgttggcttctattgtataagtggacaattagctaactgttgtcaca
ggcgattgattggccgcaaattcgacgagaaggagatccaggccgacat
caagcacttcccctacaaggtcattgagaagaacggcaagcccgtcgtc
caggtccaggtcaacgccagaagaagcagttcactcccgaggagattt
ctgccatgattcttggcaagatgaaggaggttgccgagtcgtacctggg
caagaaggttacccacgccgtcgtcaccgtccctgcctacttcaacgtg
agtcttttccccgaaattcctcgaggattccaagagccatctgctaaca
gcccgataggacaaccagcgacaggccaccaaggacgccggtaccattg
ccggcttgaacgttctccgaatcgtcaacgaacccaccgctgccgctat
cgcctatggtctggacaagaccgacggtgagcgccagatcattgtctac
gatctcggtggtggtacctttgatgtttctctcctgtccattgacaatg
gcgtcttcgaggtcttggctaccgccggtgacacccaccttggtggtga
ggactttgaccagcgcattatcaactacctggccaaggcctacaacaag
aagaacaacgtcgacatctccaaggacctcaaggccatgggcaagctca
agcgtgaagccgaaaaggccaagcgtaccctctcttcccagatgagcac
tcgtatcgaaatcgaggccttcttcgagggcaacgacttctccgagact
ctcacccgggccaagttcgaggagctcaacatggacctcttcaagaaga
ccctgaagcctgtcgagcaggttctcaaggacgccaacgtcaagaagag
cgaggttgacgacatcgttctggtcggcggttccacccgtatccccaag
gttcagtctcttatcgaggagtactttaacggcaagaaggcttccaagg
gtatcaaccccgacgaggctgttgctttcggtgccgccgtccaggccgg
tgtcctttctggtgaggaaggtaccgatgacattgttctcatggacgtc
aacccccctgactctcggtatcgagaccactggcggagtcatgaccaagc
tcattccccgcaacaccccatcccactcgcaagagccagatcttctc
gactgctgccgataaccagcccgtcgtcctgatccaggtcttcgagggt
gagcgttccatgaccaaggacaacaacctcctgggcaagttcgagctta -continued ccggcattcctcctgcccccccgcggtgtcccccagattgaggtttcctt
cgagttggatgccaacggtatcctcaaggtctccgctcacgacaagggc
accggcaagcaggagtccatcaccatcaccaacgacaagggccgtctca
cccaggaggagattgaccgcatggttgccgaggccgagaagttcgccga
ggaggacaaggctacccgtgagcgcatcgaggcccgtaacggtcttgag
aactacgccttcagcctgaagaaccaggtcaatgacgaggagggcctcg
gcggcaagattgacgaggaggacaaggagactgtaagttgaagcgatcc
atcactgctttctgatgcggacatgtcacactaacacttgaccagattc
ttgacgccgtcaaggaggctaccgagtggctcgaggagaacggcgccga
cgccactaccgaggactttgaggagcagaaggagaagctgtccaacgtc
gcctaccccatcacctccaagatgtaccagggtgctggtggctccgagg
acgatggcgacttccacgacgaattgtaaaaaattaaaaaaagggaaat
tattgatgcatagatacttattagaggaaccaaagaagttcccaggtgt
tatcgtcggttatgacgcggatgtgttttcagtcttgtaaagttcgaat
gcagctctgagtgtagtagatgcataaatgaatc SEQ ID No: 6

ATGGCGTTCCAGCAGTCGTCTCCCCTCGTCAAGTTTGAGGCCTCTCCC
GCCGAATCCTTCCTCTCCGCCCCCGGCGACAACTTCACATCCCTCTTCG
CCGACTCAACACCCTCAACACTTAACCCTCGGGACATGATGACCCCTGA
CAGCGTCGCCGACATCGACTCTCGCCTGTCCGTCATCCCCGAATCACAG
GACGCGGAAGATGACGAATCACACTCCACATCCGCTACCGCACCCTCTA
CCTCAGAAAAGAAGCCCGTCAAGAAGAGGAAATCATGGGGCCAGGTTCT
TCCTGAGCCCAAGACCAACCTCCCTCCTCGAAAACGTGCAAAGACGGAA
GATGAAAAGGAGCAGCGCCGCGTCGAGCGTGTTCTCCGCAACCGCCGCG
CCGCGCAGTCCTCGCGCGAGCGCAAGAGGCTCGAGGTCGAGGCTCTCGA
GAAGCGCAACAAGGAGCTCGAGACGCTCCTCATCAACGTCCAGAAGACC
AACCTGATCCTCGTCGAGGAGCTCAACCGCTTCCGACGCAGCTCAGGCG
TCGTCACCCGCTCGTCCTCCCCCCTCGACTCTCTCCAGGACAGCATCAC
TCTCTCCCAGCAACTCTTTTGGCTCGCGGGATGGCCAAACCATGTCCAAC
CCCGAGCAGTCCTTGATGGACCAGATCATGAGATCTGCCGCTAACCCTA
CCGTTAACCCGGCCTCTCTTTCCCCCTCCCTCCCCCCCATCTCGGACAA
GGAGTTCCAGACCAAGGAGGAGGACGAGGAACAGGCCGACGAAGATGAA
GAGATGGAGCAGACATGGCACGAGACCAAAGAAGCCGCCGCCGCCAAGG
AGAAGAACAGCAAGCAGTCCCGCGTCTCCACTGATTCGACACAACGTCC
TGCAGTGTCAATCGGTGGAGATGCCGCTGTCCCTGTCTTCTCAGACGAC
GCCGGCGCAAACTGCCTTGGCCTGGACCCTGTTCATCAGGATGATGGTC
CTTTCAGCATCGGCCATTCTTTCGGCCTGTCAGCGGCCCTTGATGCAGA
TCGCTATCTCCTGAAAGCCAACTTCTCGCTTCGCCCAACGCCTCAACT
GTTGACGACGATTATCTGGCTGGTGACTCTGCCGCCTGCTTCACGAATC
CTCTCCCCTCCGACTACGACTTCGACATCAACGACTTCCTCACAGACGA
CGCAAACCACGCCGCCTATGACATTGTGGCAGCGAGCAACTATGCCGCT

-continued

```
GCGGACCGCGAGCTCGACCTCGAGATCCACGACCCTGAGAATCAGATCC

CTTCGCGACATTCTATCCAGCAGCCCCAGTCTGGCGCGTCCTCTCATGG

ATGCGACGATGGCGGCATTGCGGTTGGTGTCTGA
```

In a yet preferred embodiment of the present invention, according to the method, *Agrobacterium tumefaciens* is applied to mediate the recombinant strain and construct a gene mutant library of the recombinant strain in the step (3).

In a yet preferred embodiment of the present invention, Ti plasmid connected to pry4 gene as the screening marker gene is selected as the skeleton plasmid in step (3), wherein the said pry4 gene encodes nutrition selective marker lactide-5'-monophosphate decarboxylase, and has the nucleotide sequence of SEQ ID NO:7he is pyr4, which is the gene of.

SEQ ID No: 7
```
gactgaccccccggttgggccctcgtcccgtctccaacagagcacca ccagacaaagaccccctgcccgcgcgaatccagacccccccagcaattcc gggcctcgttgatcctcctctactgtagttgtacatacatacctaccga ctgcattgcattggtacagctgcaggcacttccaggcacggccaccaaa ttgcagcggccttgcttgcttgcttggttcgagaactaggatctgtgt cttttgccttgccttgtcttgtctgggttcctgctcgtctgcggcaatc ggaacgccgcagtgcggtgccaagcaaaccagccaaggtaggtaccta ccactaggcttcttttctcgttgtctcactctctcttttcctctttgtc ctctcttatccccatcttttctctctctctctgctcctttcctaaccac ttccctacctttctcttttccttttcttgtcatctccatcttggctga cgaaaaggtctgactgggtaggtattatctggcagacttgtgtgtatc attcaccctatttctgcttcatagtacatgtactgtacctgaacggctc aaccgctatttacgactcttatttttttgtggcgttggtcacgtttgcc agctgttgtccgtctttctagggctcctcaaacttgacctgaccgagct ccctttctggacccggtgggcttcacttccagctgctgagcgacctgag ccgaacatcctcagtccttgtccagcgcaattcattttctttccttttc tttttttttattcctttctttacttttattctctcttttttctcctcttc ctcttcttcttctttctcctcctcctccatatcctcactctcgtctccc tcattactaccctctcggctcctcaggtccaccaaccctcccgcaccca aacctctgccgctgaaacccattcggtggtcgccgttttttttttttt ttctcaccccccaaagtcgcaatatcgggtatcgccgccggcattgaatc gccttctccgctagcatcgactactgctgctctgctctcgttgccagcg ctgctccctagaattttgaccaggggacgagcccgacattaaagcaact ccctcgcctcgagacgactcggatcgcacgaaattctcccaatcgccga cagttcctactcctcttcctcccgcacggctgtcgcgcttccaacgtca ttcgcacagcagaattgtgccatctctctctttttttcccccccctcta aaccgccacaacggcaccctaagggttaaactatccaaccagccgcagc ctcagcctctctcagcctcatcagccatggcaccacacccgacgctcaa ggccaccttcgcggccaggagcgagacggcgacgcacccgctgacggct tacctgttcaagctcatggacctcaaggcgtccaacctgtgcctgagcg ccgacgtgccgacagcgcgcgagctgctgtacctggccgacaagattgg cccgtcgattgtcgtgctcaagacgcactacgacatggtctcgggctgg gacttccaccggagacgggcacgggagcccagctggcgtcgctggcgc gcaagcacggcttcctcatcttcgaggaccgcaagtttggcgacattgg ccacaccgtcgagctgcagtacacgggcgggtcggcgcgcatcatcgac tgggcgcacattgtcaacgtcaacatggtgcccggcaaggcgtcggtgg cctcgctggcccagggcgccaagcgctggctcgagcgctacccctgcga ggtcaagacgtccgtcaccgtcggcacgccaccatggactcgtttgac gacgacgccgactccagggacgccgagcccgccggcgccgtcaacggca tgggctccattggcgtcctggacaagcccatccactcgaaccggtccgg cgacggccgcaagggcagcatcgtctccatcaccaccgtcacccagcag tacgagtccgtctcctcgcccggttaacaaaggccatcgccgagggcg acgagtcgctcttcccgggcatcgaggaggcgccgctgagccgcggcct cctgatcctcgcccaaatgtccagccagggcaacttcatgaacaaggag tacacgcaggcctgcgtcgaggccgccggggagcacaaggactttgtca tgggcttcatctcgcaggagacgctcaacaccgagcccgacgatgcctt tatccacatgacgcccggctgccagctgcccccccgaagacgaggaccag cagaccaacggatcggtcggtggagacggccagggccagcagtacaaca cgccgcacaagctgattggcatcgccggtagcgacattgccattgtggg ccggggcatcctcaaggcctcagaccccgtagaggaggcagagcggtac cgatcagcagcgtggaaagcctacaccgagaggctgctgcgataggga gggaagggaagaaagaagtaaagaaaggcatttagcaagaaggggaaa agggagggaggacaaacggagctgagaaagagctcttgtccaaagcccg gcatcatagaatgcagctgtatttaggcgacctcttttttccatcttgtc gatttttgttatgacgtaccagttgggatgatggatgattgtaccccag ctgcgattgatgtgtatctttgcatgcaacaacacgcgatggcggaggc gaactgcacattggaaggttcatatatggtcctgacatatctggtggat ctggaagcatggaattgtattttgatttggcatttgcttttgcgcgtg gagggaacatatcaccctcgggcattttttcatttggtaggatggtttgg atgcagttgatcgataagcttgatatcg
```

The present invention also provides a method for rapidly screening to the protein secretion pathway related gene for improving cellulase activity including the steps of (1) constructing the recombinant expression vector of the fusion gene DsRed-AfMp1 comprising red fluorescent protein gene and cell surface protein anchor signal peptide gene, wherein of gene DsRed has the nucleotide sequence SEQ ID No: 2, and gene AfMp1 has the nucleotide sequence of SEQ ID No: 3;

(2) transforming the strain with the recombinant vector constructed in the step (1) to obtain the recombinant strain;

(3) introducing the target gene to be screened or inserting the vectors or genes randomly into the recombinant strain obtained in the step (2) to obtain the mutant library of recombinant strain;

(4) screening of recombinant strain strongly showing the red fluorescence on its surface by flow cytometry;

(5) determining the cellulase activity of recombinant strain showing red fluorescence on its surface selected in the step (4) to obtain the recombinant strain with the improved cellulase activity; and (6) identifying the exogenous target gene or the disturbed endogenous gene in the recombinant strain with the improved cellulase activity, so as to obtain the protein secretion pathway related genes related to the improvement of cellulase activity.

The beneficial effects of the present invention are as follows:

The present invention provides the recombinant expression vector containing the fusion gene expression cassette comprising cbh1 promoter, cbh1 gene signal peptide sequence, red fluorescent protein gene, MP1 anchor protein signal peptide sequence and cbh1 gene terminator connected in order from upstream to downstream, and capable of inducing to display fluorescence on the surface of the strain so as to be rapidly screened.

And, the present invention provides a method for rapidly screening recombinant Trichoderma reesei with high expression of cellulase, identifying the expression ability of cellulase according to the red fluorescence intensity of recombinant Trichoderma reesei, wherein the higher the red fluorescence intensity, the stronger the expression ability of the recombinant Trichoderma reesei. In order to relate the expression of DsRed with the expression of T. reesei cellulase, DsRed gene is placed under the control of cellulase promoter. In particularly, the DsRed gene is connected to the downstream of the promoter strongly inducing CBH1 since it is the highest cellulase expressed in Trichoderma reesei, accounting for 50-60% of the secreted protein. Therefore, the red depth is positively correlated with the degree of cbh1 promoter induction and the Trichoderma reesei strains with high-yield of cellulase are hight-throughput screened by coupling the DsRed with the flow cytometry. Furthermore, it has been demonstrated by the results that the red fluorescent protein with the signal peptide could be effectively anchored to the cell wall, so the higher the intensity of red fluorescence, the higher the cellulase expression ability of recombinant T. reesei, the fluorescence intensity of red fluorescent protein can well represent the expression of cellulose, and the fluorescence intensity of red fluorescent protein on cell wall was positively correlated with the secretion of cellulase in fermentation broth.

BRIEF DESCRIPTIONS OF THE DRAWINGS

FIG. 4 shows the colony PCR results of the secretory pathway related transformants, wherein FIG. 4-1 is hac1 colony PCR, FIG. 4-2 is bip1 colony PCR, FIG. 4-3 is ypt1 colony PCR, FIG. 4-4 is sso2 colony PCR, FIG. 4-5 is sar1 colony PCR, and FIG. 4-6 is ftt1 colony PCR;

FIG. 5 shows the results of determining EG enzyme activity in the shake flask fermentation broth of the original strain and the transformants related to secretion pathway;

FIG. 6 is the copy number identification map of the transformants related to the modifying secretion pathway;

EMBODIMENT

The invention is further described in detail in combination with the drawings, so that those skilled in the art can implement it with reference to the description.

The experimental methods used in the following embodiments are conventional methods unless otherwise specified.

The materials, reagents, etc. used in the following embodiments can be obtained from commercial sources without special instructions.

The ingredients of the MM medium in the following embodiment include $(NH_4)_2SO_4$ in the concentration of 5.0 g/L, $KH_2PO_4$ in the concentration of 15.0 g/L, $MgSO_4 \cdot 7H_2O$ in the concentration of 0.6 g/L, $CaCl_2 \cdot 2H_2O$ in the concentration of 0.6 g/L, $CoCl_2 \cdot 6H_2O$ in the concentration of 0.0037 g/L, $FeSO_4 \cdot 7H_2O$ in the concentration of 0.005 g/L, $ZnSO_4 \cdot 7H_2O$ in the concentration of 0.0014 g/L, $MnSO_4 \cdot H_2O$ in the concentration of 0.0016 g/L, glucose or carbon sources such as Avicel in the concentration of 20 g/L and the water as the solvent used.

Example 1 Display of Red Fluorescent Protein on the Surface of Tichoderma reesei Cells 1. Constructing the recombinant plasmid pdsRed-AfMP1 expressing the fusion gene DsRed-AfMP1 of the red fluorescent protein and Aspergillus fumigatus cell surface protein anchored signal peptide DsRed gene fragment was amplified from plasmid DsRed with the F-terminal primer comprising cbh1 gene signal peptide sequence of 51 bp, AfMP1 gene fragment was amplified from plasmid AfMP1, and the two fragments were connected by overlap PCR.

Cbh1 promoter and terminator were amplified from the genome of T. reesei Tu6 to construct the expression cassette cbh1p-DsRed-AfMp-cbh1t, while being seamlessly spliced to the linearized pAPA plasmid and cbh1p-DsRed-AfMp-cbh1t expression cassette by homologous recombination in vivo, and then transformed into E. coli, following by selecting the positive transformants and extracting the plasmids.

2. Expression of fusion gene pDsRed-AfMp1 in Trichoderma reesei SUS2

Trichoderma reesei SUS2 was inoculated on potato culture medium (PDA) plate, and incubated for 7 days at 30C until forming spores which were scraped off and inoculated into 100 mL of PDB medium containing uridine, followed by shaking overnight at 30° C. and 180 rpm. The germinating hyphae were collected by filtration with 12 layers of gauze and digested at 30° C. for 1 to 2 hours with 10 mg/mL of yeast breaking-wall enzyme to collect the protoplasts. And, pDsRed-AfMp1 plasmid was transformed into Trichoderma reesei SUS2 strain by PEG mediated protoplast transformation.

Figure 1:
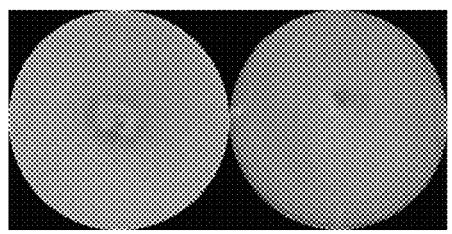
FIG. 1 shows the colony of Trichoderma reesei., wherein the left picture shows the original strain SUS2, and the right picture shows the positive transformant SUS4 transferred into pDsRed-AfMP1 plasmid.

The transformants were grown and selected on MM-glucose agar medium containing 1 M sorbitol. The single clone was selected and inoculated on MM-lactose agar medium for 5 days in the incubator at 30° C. to observe the color change. As shown in FIG. 1, there is the red fluorescent protein which can by observed with the naked eye, displayed on the surface of the positive transformants successfully transforming and expressing pDsRed-AfMp1 plasmid, named as SUS4.

Figure 2:
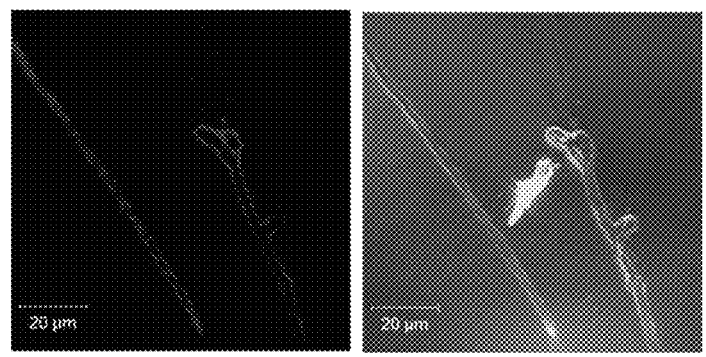
FIG. 2 shows the Trichoderma reesei hyphae under the fluorescence microscope, wherein the left picture shows the Trichoderma reesei hyphae displaying the red fluorescent protein on its surface, and the right picture shows the Trichoderma reesei hyphae observed under the fluorescent microscope in the bright field.

As shown in FIG. 2, the red fluorescent protein expressed on the cell surface of the obtained transformant can be observed under the confocal microscope, after being cultured in MM-Avicel for 24 hours.

Example 2 Screening of Cellulase with High Cellulase Activity

1. Expression of *Trichoderma reesei*'s protein secretion pathway related genes in *Trichoderma reesei* SUS4

Six gene fragments related to the secretion pathway of *Trichoderma reesei*, bip1 gene, hac1 gene, ftt1 gene, sso2 gene, sar1 gene, and ypt1 gene, were selected and connected with the appropriate promoters and terminators to construct the expression cassettes enolp-bip1-eno1t, enolp-hac1-eno1t, pdc1p-ftt1-pdc1t, pdc1p-sso2-pdc1t, gpd1p-sar1-gpd1t, and gpd1p-ypt1-gpd1t respectively.

And, the six secretory pathway related recombinant plasmids, i.e., pAPA-eno1-bip1, pAPA-eno1-hac1, pAPA-pdc1-sso2, pAPA-pdc1-ftt1, pAPA-gpd1-sar1 and pAPA-gpd1-ypt1, were constructed by linearizing plasmid pAPA and seamless splicing with the above six gene fragments at a molar ratio of 1:2. The obtained recombinant plasmids were transformed into *E. coli* T competent cells, and colony PCR was performed to identify whether the six fragments were connected to the pAPA. The positive colonies identified by PCR were selected and inoculated into 1 mL of LB medium containing 100 μg/mL of ampicillin for shaking culture overnight at 37'C and 220 rpm to extract the plasmids for transformation The above six secretion pathways related plasmids were mixed in equal volume and then transformed into *Trichoderma reesei* SUS4 strain by PEG mediated protoplast transformation.

The obtained transformants were selected and cultured on PDA at 28° C. until producing spores, wherein four transformants can be selected from each plate. 8 mL of sterile water was used to wash the spores of all transformants on the plate, and then the spores were evenly suspended at $10^6$ to $10^8$ spores, followed by being filtered into the sterile tip bottom centrifuge tube with the 200 mesh sieve, for being analyzed and sorted by flow cytometry.

Figure 3:
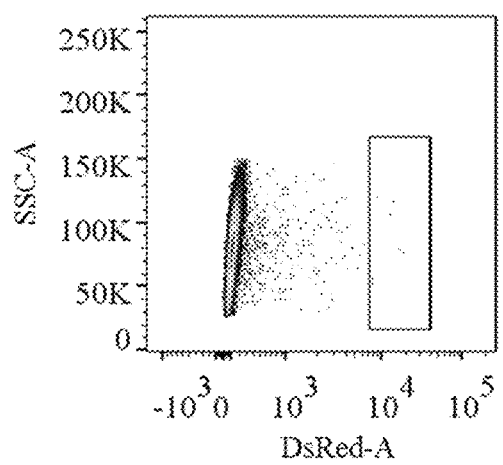
FIG. 3 is the flow cytometry sorting diagram of plasmid transformants related to secretory pathway.

Flow cytometry was used to analyze the sporozoites of the transformants with the sample pressure of 1000 EPS, i.e. 1000 signal particles per second, wherein the area and width map of forward angle scattering light was used to remove the adhesion and miscellaneous signals, the fluorescence signal was excited by 488 nm of laser, the voltage was set by the negative control strain expressing RFP to distinguish the expressed sporozoites, and the positive spore region was determined according to the signal difference between the positive and negative spores. All samples were analyzed in the same way. The spores with the strongest fluorescence signal were directly sorted into the 6-well plate containing PDA, and the total 36 transformants were sorted and cultured until producing the spores, as shown the flow sorting diagram of FIG. 3.

The selected transformants were inoculated in 25 mL of liquid MM-glucose and shaken at 30° C. and 180 rpm for 1 day. Genomic DNA was extracted and PCR was used to verify whether the recombinant plasmids were successfully transformed into *Trichoderma reesei* cells.

Figure 4:
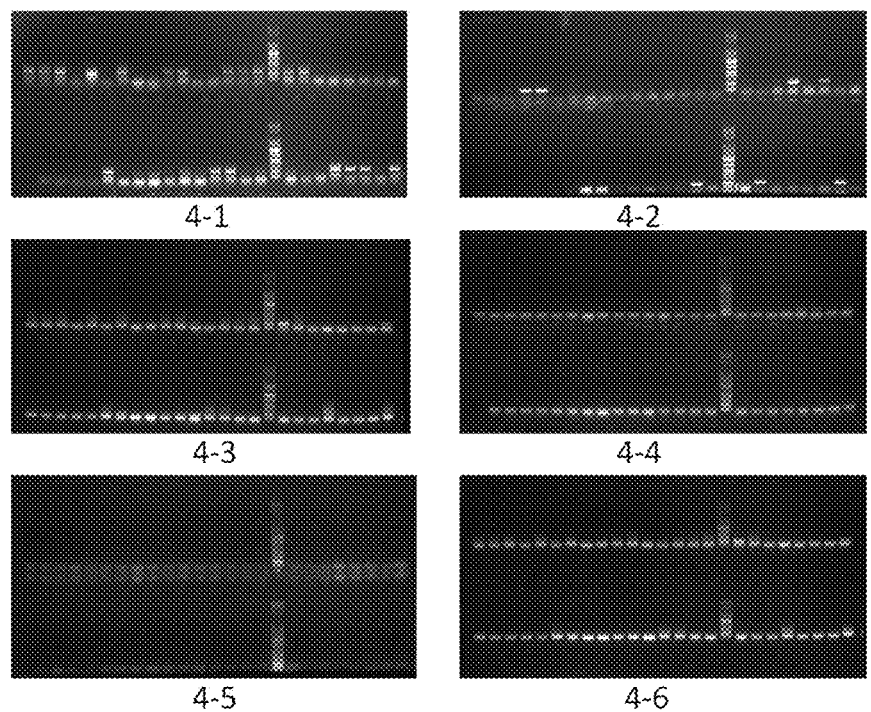

The transformants screened by flow cytometry were used for colony PCR with 6 pairs of primers related to secretion pathway to determine what kind of secretion pathway related plasmids were contained in the selected transformants with the enhanced red fluorescence. The primers used are shown in the table below, the PCR fragment size is about 200 bp, and the electrophoresis results are shown in FIG. 4.

TABLE 1

Primer sequence

| Primer | 5'→3' | Usage |
|---|---|---|
| Peno (F) | GGCTTCACTTTCGATGTCGT | Screening of bip1 and hac1 transformants |
| Pbip1 (R) | GTTGAGGGGGGGTATCTTTG | Screening of bip1 transformants |
| Phac1 (R) | TTGAGTCGGCGAAGAGGGAT | Screening of hac1 transformants |
| Pgpd (F) | CTCCTCCCTCTCTCCCTCTC | Screening of sar1 and ypt1 transformants |
| Psar1 (R) | TCGCATCAGGTAAGCTGTTG | Screening of sar1 transformants |
| Pypt1 (R) | GCAATCAAGCGACGGAGGAC | Screening of ypt1 transformants |
| Ppdc (F) | AGAGTGTCGTCACCAGTATA | Screening of ftt1 and sso2 transformants |
| Pftt1 (R) | GACGGGAGGGAGGATACGTA | Screening of ftt1 transformants |
| Psso2 (R) | AAGGAGCCATCTCTACTGCG | Screening of sso2 transformants |

As shown in FIG. 4, 31 transformants were obtained by colony PCR from the 36 transformants screened by flow cytometry, of which 22 transformants comprised hac1 gene and 9 transformants contained bip1 gene, being confirmed by sequencing, whereas the other four secretion pathway related plasmid sequences were not amplified.

The results showed that hac1 gene and bip1 gene could enhance the cellulase production ability of DsRed-AfMP1 transformants, whereas the overexpression of the other four secretion related genes could not promote the cellulase secretion and expression under the present strain and culture conditions.

2. Determination of cellulase activity of the recombinant plasmid transformants related to secretion (1) Inducing and culturing the selected transformants $1\times10^7$ spores screened from the spores of the original strain and spores separated by flow cytometry were inoculated into 100 mL of MM-glucose medium, for shaking culture at 30° C. and 180 rpm for 1 day, the mycelium was filtered with 12 layers of gauze, collected and washed with a large amount of sterile water to remove the residual glucose.

500 mg of mycelium was weighed in the same amount and inoculated in 100 mL of MM-Avicel liquid medium, wherein the original strain and each transformant were set in three parallels, to induce cellulase production by shaking at 30° C. and 180 rpm for 168 h wherein the fermentation broth was collected every 24 h since 72h and stored in a refrigerator at 4° C. for standby.

(2) Determining cellulase activity

Extraction of Cellulase 2 mL of fermentation broth collected in each time period was centrifuged at 8000 rpm to obtain the supernatant.

Determination of Cellulase Activity

The enzyme activities of the original strain SUS4 and the 31 transformants identified by colony PCR were determined, wherein the fermentation broth from 3 to 6 d was taken to determine the activity of endocellulase (CMC enzyme activity).

Sodium carboxymethyl cellulose (CMC) was used as the substrate for determining endocellulase activity by adding citric acid disodium hydrogen phosphate buffer in 0.05 M with pH 5.0 to 1000 mg of sodium carboxymethyl cellulose until 50 mL to obtain 2% sodium carboxymethyl cellulose solution.

And, the enzyme activity of endocellulase was determined by adding 100 μL of enzyme solution into 10 mL of citric acid disodium hydrogen phosphate buffer in 0.05 M with pH 5.0 to obtain the enzyme solution diluted 101 times, adding 2% of sodium carboxymethyl cellulose solution and citric acid disodium hydrogen phosphate buffer solution of 0.45 mL to each tube respectively, inin water bath equilibrium at 50° C., adding 0.1 mL of the diluted enzyme solution wherein the blank wasn't added, for shaking and mixing evenly to be kept in water bath at 50° C. for 30 min and rapid cooling, followed by adding 1.5 mL of DNS reagent to each test tube, adding 0.1 mL enzyme solution to the blank, and mixing evenly for putting into boiling water for 10 minutes and cooling quickly, so as to determine the absorbance at 540 nm taking No. 0 tube as reference, wherein the amount of enzyme required to hydrolyze sodium carboxymethyl cellulose to produce 1 μmol reducing sugar (glucose) per hour at 50° C. and pH 5.0 by 1 mL of liquid enzyme was defined as one enzyme activity unit (U).

Figure 5:
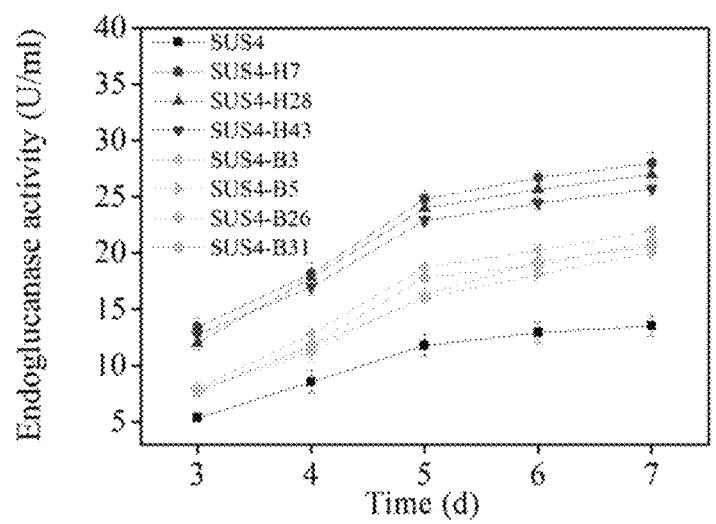

The enzyme activity test results are shown in FIG. 5, wherein the enzyme activity of seven transformants was improved, including three transformants containing hac1 gene, named as SUS4-H7, SUS4-H28, and SUS4-H43 respectively, and four transformants with bip gene, named as SUS4-B3, SUS4-B5, SUS4-B26 and SUS4-B31respectively.

3. Identification of copy number of transformants

The qRT PCR was used to identify the copy number of transformants taking 1 μl of diluted temple and the primer as below, wherein the genomes of the above transformants were selected as template and diluted 5 times, and actin gene was used as internal reference gene RTQactF
(5'-TGAGAGCGGTGGTATCCACG-3')

RTQactR
(5'-GGTACCACCAGACATGACAATGTTG-3')

RTQbacF
(5'-ACAACGTCCTGCAGTGTCAA-3')

RTQbacR
(5'-TAGCGATCTGCATCAAGGGC-3')

RTQbipF
(5'-AAGAAGGTTACCCACGCCG-3')

RTQbipR
(5'-ATCAAAGGTACCACCACCGAG-3')

Figure 6:
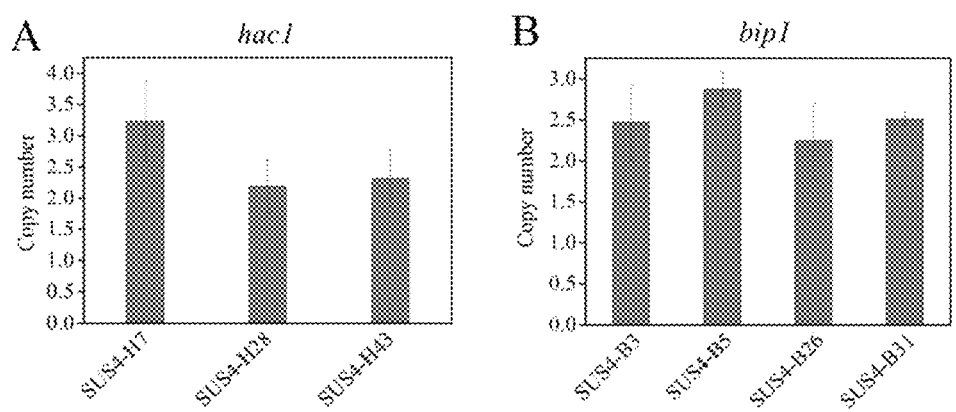

The copy number of Bgl3p1 gene was quantified by $2^{-\Delta\Delta C_t}$ method, and the results of copy number identification of transformants are shown in FIG. 6A and FIG. 6B, wherein quantitative PCR analysis showed that one or two copies of HAC1 and BIP1 genes were integrated into the chromosome.

Example 3 Constructing Gene Mutant Library to Screen Transformants Highly Expressing the Cellulase with the High Activity 1. Construction of plasmid pTi-pyr4 from *Agrobacterium tumefaciens*

Pyr4 gene was amplified from *Trichoderma reesei* and the plasmid pTi-pyr4 transforming *Agrobacterium tumefaciens* was constructed.

*Agrobacterium tumefaciens* competent AGL1 was transformed with the constructed plasmid pTi-pyr4d containing a *Trichoderma* transformation screening marker gene pyr4, and left arm (LB) and right arm (RB) for *Agrobacterium tumefaciens* random insertion.

Figure 7:
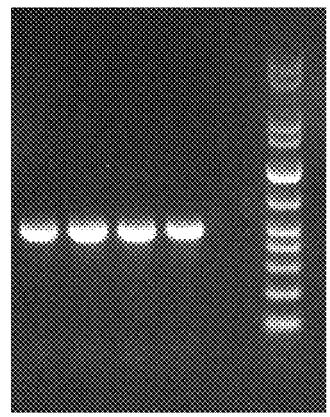
FIG. 7 shows the colony PCR results of Ti-pyr4 plasmid transformed into Agrobacterium tumefaciens.

After the transformant colony grows, the single colony was select for verifying the target gene pry4 by colony PCR. As shown in FIG. 7, the size of the amplified target fragment is 500 bp, being consistent with the size of the pre-verified fragment, and is conformed by sequencing.

2. Construction of *Agrobacterium* pTi-pyr4 random insertion mutant library of *Trichoderma reesei*

3 μL of *Agrobacterium tumefaciens*( ) transferred with the target plasmid pTi-pyr4 was inoculated into 3 mL of LB liquid containing 50 μg/mL of kanamycin and 25 μg/mL of rifampicin and cultured at 220 rpm and 28° C. in the shaking table.

Spore suspension of *Trichoderma reesei* SUS4 was prepared and coated on CM plate covered with cellophane for pre-germinating at 24° C. for about 3 h. And, 100μ 1 of *Agrobacterium tumefaciens* liquid was coated on CM plate with the pre-germinated *Trichoderma reesei* mycelium for co-culturing at 25° C. in dark to obtain *Agrobacterium tumefaciens* mediated *Trichoderma reesei* mutant library.

The normal growth colonies on the MM plate without uracil and cephalosporin were obtained after primary screening and secondary screening, and considered as the suspected transformants which were verified by PCR with the extracted genomic DNA.

Figure 8:
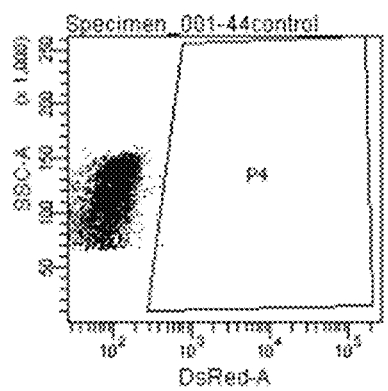
FIG. 8 shows the flow cytometry of Agrobacterium tumefaciens randomly inserted mutant library.

3. Flow cytometry sorting *Agrobacterium* pTi-pyr4 random insertion mutant library The plasmid pTi-pyr4 was transformed into the protoplast of SUS4 strain by *Agrobacterium tumefaciens* mediated transformation, so as to successfully construct the *Agrobacterium tumefaciens* transformation mutant library of which the transformants were imaged on the PDA plate containing cephalosporin through membrane transfer. As shown in FIG. 8, the *Trichoderma reesei* strains showing the red fluorescence on the surface were screened by flow cytometry after sporulation.

Figure 9:
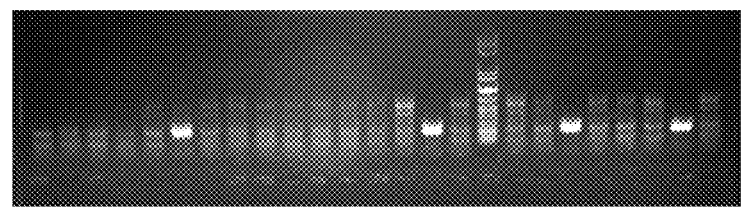
FIG. 9 shows the result of PCR validation of the randomly inserted transformant colonies of Agrobacterium tumefaciens screened by the flow cytometry.

Primers were used to verify whether the transformant screened by flow cytometry comprised plasmid pTi-pry4, wherein as shown in FIG. 9, the results showed that four transformants after transforming the stain SUS4 were screened and confirmed to contain said plasmid, named as SUS4-T7, SUS4-T33, SUS4-T37 and SUS4-T47.

Figure 10:
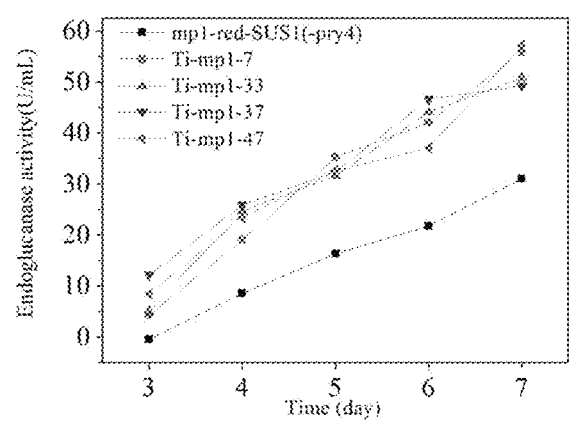
FIG. 10 shows the enzyme activity of Agrobacterium tumefaciens randomly inserted transformants.

4. Enzyme activity analysis of *Agrobacterium tumefaciens* pTi-pyr4 randomly inserted transformants screened by flow cytometry The transformants screened by flow cytometry were analyzed by shake flask fermentation taking SUS4 as the control strain. After MM and Avicel inducing, samples were taken to determine the CMC-Na activity in the supernatant. As shown in FIG. 10, the endoglucanase activities of the four transformants found by shake flask fermentation were 26.3-33.3 U/mL higher than that of their parents which is 11.1 U/ml.

The invention claimed is:

1. A recombinant expression vector for rapidly screening *Trichoderma reesei* with enhanced expression or activity of cellulase comprising a gene expression cassette comprising a cbh1 promoter, a red fluorescent protein gene DsRed, a cell surface protein anchor signal peptide gene AfMp1 and a cbh1 terminator in order from upstream to downstream, respectively wherein said DsRed gene has the nucleotide sequence of SEQ ID No: 2, and said AfMp1 gene has the nucleotide sequence of SEQ ID No: 3.

2. A method for the rapidly screening *Trichoderma reesei* with enhanced expression or activity of cellulase including the steps of:
   (1) introducing a gene expression cassette comprising a cbh1 promoter, a red fluorescent protein gene DsRed, a cell surface protein anchor signal peptide gene AfMp1 and a cbh1 terminator, into the plasmid to obtain a recombinant expression vector, wherein said DsRed gene has the nucleotide sequence of SEQ ID No: 2, and said AfMp1 gene has the nucleotide sequence of SEQ ID No: 3;
   (2) transforming a *Trichoderma reesei* cell with the recombinant vector constructed in step (1) to obtain a recombinant *Trichoderma reesei*;
   (3) introducing a protein secretion pathway related gene or into the recombinant *Trichoderma reesei* obtained in step 2 to obtain a mutant library of the recombinant *Trichoderma reesei*;
   (4) screening of the recombinant *Trichoderma reesei* mutant library from part (4) and selecting those that show red fluorescence on its surface as determined by flow cytometry; and
   (5) determining the cellulase activity of the recombinant *Trichoderma reesei* obtained in step (4), to obtain the recombinant *Trichoderma reesei* with enhanced expression or activity of cellulase.

3. The method for rapidly screening *Trichoderma reesei* highly expressing with enhanced expression or activity of cellulase according to claim 2, wherein in the step 3, said protein secretion pathway related genes includes bip1 gene, hac1 gene, fit1 gene, sso2 gene, sar1 gene or ypt1 gene.

4. The method for rapidly screening *Trichoderma reesei* with enhanced expression or activity of cellulase according to claim 2, wherein in the step 3, *Agrobacterium tumefaciens* mediates transformation of *Trichoderma reesei* to obtain said mutant library of the recombinant *Trichoderma reesei*.

* * * * *

SEQUENCE LISTING

```
<160> NUMBER OF SEQ ID NOS: 22

<210> SEQ ID NO 1
<211> LENGTH: 1193
<212> TYPE: DNA
<213> ORGANISM: Artificial Sequence
<220> FEATURE:
<223> OTHER INFORMATION: synthesized promoter

<400> SEQUENCE: 1
tcaacctttg gcgtttccct gattcagcgt acccgtacaa gtcgtaatca ctattaaccc      60
agactgaccg gacgtgtttt gcccttcatt tggagaaata atgtcattgc gatgtgtaat     120
ttgcctgctt gaccgactgg ggctgttcga agcccgaatg taggattgtt atccgaactc     180
tgctcgtaga ggcatgttgt gaatctgtgt cgggcaggac acgcctcgaa ggttcacggc     240
aagggaaacc accgatagca gtgtctagta gcaacctgta aagccgcaat gcagcatcac     300
tggaaaatac aaaccaatgg ctaaaagtac ataagttaat gcctaaagaa gtcatatacc     360
agcggctaat aattgtacaa tcaagtggct aaacgtaccg taatttgcca acggcttgtg     420
gggttgcaga agcaacggca aagccccact tccccacgtt tgtttcttca ctcagtccaa     480
tctcagctgg tgatccccca attgggtcgc ttgtttgttc cggtgaagtg aaagaagaca     540
gaggtaagaa tgtctgactc ggagcgtttt gcatacaacc aagggcagtg atggaagaca     600
gtgaaatgtt gacattcaag gagtatttag ccagggatgc ttgagtgtat cgtgtaagga     660
ggtttgtctg ccgatacgac gaatactgta tagtcacttc tgatgaagtg gtccatattg     720
aaatgtaagt cggcactgaa caggcaaaag attgagttga aactgcctaa gatctcgggc     780
cctcgggcct tcggcctttg ggtgtacatg tttgtgctcc gggcaaatgc aaagtgtggt     840
aggatcgaac acactgctgc ctttaccaag cagctgaggg tatgtgatag gcaaatgttc     900 agggggccact gcatggtttc gaatagaaag agaagcttag ccaagaacaa tagccgataa     960
agatagcctc attaaacgga atgagctagt aggcaaagtc agcgaatgtg tatatataaa    1020
ggttcgaggt ccgtgcctcc ctcatgctct ccccatctac tcatcaactc agatcctcca    1080
ggagacttgt acaccatctt ttgaggcaca gaaacccaat agtcaaccgc ggactgcgca    1140
tcatgtatcg gaagttggcc gtcatctcgg ccttcttggc cacagctcgt gct           1193

<210> SEQ ID NO 2
<211> LENGTH: 153
<212> TYPE: DNA
<213> ORGANISM: Artificial Sequence
<220> FEATURE:
<223> OTHER INFORMATION: synthesized gene

<400> SEQUENCE: 2
ggcggctccg gctccggctc cggctccagc actggtactg ccactgcctc caccagcacc       60
```

```
aacctcctca agactggcgc cgccagcaag gagcacttca gctactccct cggcggtgcc    120
gtcgtcgcgg ccgccatcgc cgtcgctctc taa                                 153
```

<210> SEQ ID NO 3
<211> LENGTH: 675
<212> TYPE: DNA
<213> ORGANISM: Artificial Sequence
<220> FEATURE:
<223> OTHER INFORMATION: synthesized gene

<400> SEQUENCE: 3

```
atggacaaca ccgaggacgt catcaaggag ttcatgcagt tcaaggtgcg catggagggc     60
tccgtgaacg gccactactt cgagatcgag ggcgagggcg agggcaagcc ctacgagggc    120
acccagaccg ccaagctgca ggtgaccaag ggcggccccc tgcccttcgc ctgggacatc    180
ctgtcccccc agttccagta cggctccaag gcctacgtga agcaccccgc cgacatcccc    240
gactacatga agctgtcctt ccccgagggc ttcacctggg agcgctccat gaacttcgag    300
gacggcggcg tggtggaggt gcagcaggac tcctccctgc aggacggcac cttcatctac    360
aaggtgaagt tcaagggcgt gaacttcccc gccgacggcc ccgtaatgca gaagaagact    420
gccggctggg agcctccac cgagaagctg taccccagg acggcgtgct gaagggcgag    480
atctcccacg ccctgaagct gaaggacggc ggccactaca cctgcgactt caagaccgtg    540
tacaaggcca gaagcccgt gcagctgccc ggcaaccact acgtggactc caagctggac    600
atcaccaacc acaacgagga ctacaccgtg gtggggcagt acgagcacgc cgaggcccgc    660
cactccggct cccag                                                    675
```

<210> SEQ ID NO 4
<211> LENGTH: 500
<212> TYPE: DNA
<213> ORGANISM: Artificial Sequence
<220> FEATURE:
<223> OTHER INFORMATION: synthesized terminator

<400> SEQUENCE: 4

```
agctccgtgg cgaaagcctg acgcaccggt agattcttgg tgagcccgta tcatgacggc     60
ggcgggagct acatggcccc gggtgattta tttttttttgt atctacttct gacccttttc    120
aaatatacgg tcaactcatc tttcactgga gatgcggcct gcttggtatt gcatgttgt    180 cagcttggca aattgtggct ttcgaaaaca caaaacgatt ccttagtagc catgcatttt    240
aagataacgg aatagaagaa agaggaaatt aaaaaaaaaa aaaaaacaaa catcccgttc    300
ataacccgta gaatcgccgc tcttcgtgta tcccagtacc acggcaaagg tatttcatga    360
tcgttcaatg ttgatattgt tcccgccagt atggctccac ccccatctcc gcgaatctcc    420
tcttctcgaa cgcggtagtg gcgcgccaat tggtaatgac ccatagggag acaaacagca    480
taatagcaac agtggaaatt                                                500
```

<210> SEQ ID NO 5
<211> LENGTH: 2680
<212> TYPE: DNA
<213> ORGANISM: Artificial Sequence
<220> FEATURE:
<223> OTHER INFORMATION: synthesized gene

<400> SEQUENCE: 5

```
ataaagtggc ccatcgtcac ctctcggctt caactcgagt ttttcccttt ttcctttct      60 tcttcttctt caaacaaaga tacccccccct caacccggtg caaccagcct ggtccgagga   120
```

```
caaaacacga tagagctcgc tgcgttggat cgctgcgcgt cttctcttgt tctctctctc    180
ttttcttctc tgcaacgctt ataactcttt ttgcgcgggg catctgggaa aaccgtttct    240
tcacacatct cttcttccac aatggctcgt tcacggagct ccctggccct cgggctgggc    300
ctgctctgct ggatcacgct gctcttcgct cctctggcgt tgtcggaaa ggccaatgcc     360 gcgagcgacg acgcggacaa ctacggcact gttatcggaa ttgtaagtcg actgacggca    420
gcaaccccgc cattttcttg gtgttgatgc tcaggcagcc ctgctaacac gcttctcctc    480
cgcccaggat ctcggaacta cctacagctg cgtcggtgtg atgcagaagg caaggttga    540 gattctcgtc aacgaccagg gtaaccgaat cactccctcc tacgtggcct ttaccgacga    600
ggagcgtctg gttggcgatt ccgccaagaa ccaggccgcc gccaaccccca caacaccgt     660 ctacgatgtc aagtcagttc taccgccctg ttggcttcta ttgtataagt ggacaattag    720
ctaactgttg tcacaggcga ttgattggcc gcaaattcga cgagaaggag atccaggccg    780
acatcaagca cttcccctac aaggtcattg agaagaacgg caagcccgtc gtccaggtcc    840
aggtcaacgg ccagaagaag cagttcactc ccgaggagat ttctgccatg attcttggca    900
agatgaagga ggttgccgag tcgtacctgg gcaagaaggt tacccacgcc gtcgtcaccg    960
tccctgccta cttcaacgtg agtctttttcc ccgaaattcc tcgaggattc caagagccat   1020
ctgctaacag cccgatagga caaccagcga caggccacca aggacgccgg taccattgcc   1080
ggcttgaacg ttctccgaat cgtcaacgaa cccaccgctg ccgctatcgc ctatggtctg    1140
gacaagaccg acggtgagcg ccagatcatt gtctacgatc tcggtggtgg tacctttgat   1200
gtttctctcc tgtccattga caatggcgtc ttcgaggtct tggctaccgc cggtgacacc    1260
caccttggtg gtgaggactt tgaccagcgc attatcaact acctggccaa ggcctacaac    1320
aagaagaaca acgtcgacat ctccaaggac ctcaaggcca tgggcaagct caagcgtgaa    1380
gccgaaaagg ccaagcgtac cctctcttcc cagatgagca ctcgtatcga aatcgaggcc    1440
ttcttcgagg gcaacgactt ctccgagact ctcacccggg ccaagttcga ggagctcaac    1500 atggaccctct tcaagaagac cctgaagcct gtcgagcagg ttctcaagga cgccaacgtc    1560
aagaagagcg aggttgacga catcgttctg gtcggcggtt ccacccgtat ccccaaggtt    1620
cagtctctta tcgaggagta ctttaacggc aagaaggctt ccaagggtat caaccccgac    1680
gaggctgttg ctttcggtgc cgccgtccag gccggtgtcc tttctggtga ggaaggtacc    1740
gatgacattg ttctcatgga cgtcaacccc ctgactctcg gtatcgagac cactggcgga    1800
gtcatgacca agctcattcc ccgcaacacc cccatcccca ctcgcaagag ccagatcttc    1860
tcgactgctg ccgataacca gcccgtcgtc ctgatccagg tcttcgaggg tgagcgttcc    1920
atgaccaagg acaacaacct cctgggcaag ttcgagctta ccggcattcc tcctgccccc    1980
cgcggtgtcc cccagattga ggtttccttc gagttggatg ccaacggtat cctcaaggtc    2040
tccgctcacg acaagggcac cggcaagcag gagtccatca ccatcaccaa cgacaagggc    2100
cgtctcaccc aggaggagat tgaccgcatg gttgccgagg ccgagaagtt cgccgaggag    2160
gacaaggcta cccgtgagcg catcgaggcc cgtaacggtc ttgagaacta cgccttcagc    2220
ctgaagaacc aggtcaatga cgaggagggc ctcggcggca agattgacga ggaggacaag    2280
gagactgtaa gttgaagcga tccatcactg cttttctgatg cggacatgtc acactaacac    2340
ttgaccagat tcttgacgcc gtcaaggagg ctaccgagtg gctcgaggag aacgcgccg     2400 acgccactac cgaggacttt gaggagcaga aggagaagct gtccaacgtc gcctacccca    2460
```

| | |
|---|---:|
| tcacctccaa gatgtaccag ggtgctggtg gctccgagga cgatggcgac ttccacgacg | 2520 |
| aattgtaaaa aattaaaaaa agggaaatta ttgatgcata gatacttatt agaggaacca | 2580 |
| aagaagttcc caggtgttat cgtcggttat gacgcggatg tgttttcagt cttgtaaagt | 2640 |
| tcgaatgcag ctctgagtgt agtagatgca taaatgaatc | 2680 |

<210> SEQ ID NO 6
<211> LENGTH: 1356
<212> TYPE: DNA
<213> ORGANISM: Artificial Sequence
<220> FEATURE:
<223> OTHER INFORMATION: synthesized gene

<400> SEQUENCE: 6

| | |
|---|---:|
| atggcgttcc agcagtcgtc tccnctcgtc aagtttgagg cctctcccgc cgaatccttc | 60 |
| ctctccgccc ccggcgacaa cttcacatcc ctcttcgccg actcaacacc ctcaacactt | 120 |
| aaccctcggg acatgatgac ccctgacagc gtcgccgaca tcgactctcg cctgtccgtc | 180 |
| atccccgaat cacaggacgc ggaagatgac gaatcacact ccacatccgc taccgcaccc | 240 |
| tctacctcag aaaagaagcc cgtcaagaag aggaaatcat ggggccaggt tcttcctgag | 300 |
| cccaagacca acctccctcc tcgaaaacgt gcaaagacgg aagatgaaaa ggagcagcgc | 360 |
| cgcgtcgagc gtgttctccg caaccgccgc gccgcgcagt cctcgcgcga gcgcaagagg | 420 |
| ctcgaggtcg aggctctcga gaagcgcaac aaggagctcg agacgctcct catcaacgtc | 480 |
| cagaagacca acctgatcct cgtcgaggag ctcaaccgct tccgacgcag ctcaggcgtc | 540 |
| gtcacccgct cgtcctcccc cctcgactct tccaggaca gcatcactct ctcccagcaa | 600 |
| ctctttggct cgcgggatgg ccaaaccatg tccaaccccg agcagtcctt gatggaccag | 660 |
| atcatggagt ctgccgctaa ccctaccgtt aacccggcct ctcttttcccc ctccctcccc | 720 |
| cccatctcgg acaaggagtt ccagaccaag gaggaggacg aggaacaggc cgacgaagat | 780 |
| gaagagatgg agcagacatg gcacgagacc aaagaagccg ccgccgccaa ggagaagaac | 840 |
| agcaagcagt cccgcgtctc cactgattcg acacaacgtc ctgcagtgtc aatcggtgga | 900 |
| gatgccgctg tccctgtctt ctcagacgac gccggcgcaa actgccttgg cctggaccct | 960 |
| gttcatcagg atgatggtcc tttcagcatc ggccattctt tcggcctgtc agcggccctt | 1020 |
| gatgcagatc gctatctcct cgaaagccaa cttctcgctt cgcccaacgc tcaactgtt | 1080 |
| gacgacgatt atctggctgg tgactctgcc gcctgcttca cgaatcctct cccctccgac | 1140 |
| tacgacttcg acatcaacga cttcctcaca gacgacgcaa accacgccgc ctatgacatt | 1200 |
| gtggcagcga gcaactatgc cgctgcggac cgcgagctcg acctcgagat ccacgaccct | 1260 |
| gagaatcaga tcccttcgcg acattctatc cagcagcccc agtctggcgc gtcctctcat | 1320 |
| ggatgcgacg atggcggcat tgcggttggt gtctga | 1356 |

<210> SEQ ID NO 7
<211> LENGTH: 2919
<212> TYPE: DNA
<213> ORGANISM: Artificial Sequence
<220> FEATURE:
<223> OTHER INFORMATION: synthesized gene

<400> SEQUENCE: 7

| | |
|---|---:|
| gactgacccc ccggttggg ccctcgtcc cgtctccaac agagcaccac cagacaaaga | 60 |
| cccctgcccg cgcgaatcca gaccccccca gcaattccgg gcctcgttga tcctcctcta | 120 |
| ctgtagttgt acatacatac ctaccgactg cattgcattg gtacagctgc aggcacttcc | 180 |

```
aggcacggcc accaaattgc agcggcccct gcttgcttgc ttggttcgag aactaggatc      240
tgtgtctttt gccttgcctt gtcttgtctg ggttcctgct cgtctgcggc aatcggaacg      300
ccgccagtgc ggtgccaagc aaaccagcca aggtaggtac ctaccactag gcttcttttc      360
tcgttgtctc actctctctt ttcctctttg tcctctctta tccccatctt ttctctctct      420
ctctgctcct ttcctaacca cttccctacc tttctctttt tccttttctt gtcatctcca      480
tcttggctga cgaaaaaggt ctgactgggt aggtattatc tggcagactt gtgtgtatca      540
ttcaccctat ttctgcttca tagtacatgt actgtacctg aacggctcaa ccgctattta      600
cgactcttat ttttttgtgg cgttggtcac gtttgccagc tgttgtccgt ctttctaggg      660
ctcctcaaac ttgacctgac cgagctccct ttctggaccc ggtgggcttc acttccagct      720
gctgagcgac ctgagccgaa catcctcagt ccttgtccag cgcaattcat tttctttcct      780
tttctttttt tttattcctt tctttacttt tattctctct ttttctcctc ttcctcttct      840
tcttctttct cctcctcctc catatcctca ctctcgtctc cctcattact accctctcgg      900
ctcctcaggt ccaccaaccc tcccgcaccc aaacctctgc cgctgaaacc cattcggtgg      960
tcgccgtttt ttttttttt ttctcacccc caaagtcgca atatcgggta tcgccgccgg     1020
cattgaatcg ccttctccgc tagcatcgac tactgctgct ctgctctcgt tgccagcgct     1080
gctccctaga attttgacca ggggacgagc ccgacattaa agcaactccc tcgcctcgag     1140
acgactcgga tcgcacgaaa ttctcccaat cgccgacagt tcctactcct cttcctcccg     1200
cacggctgtc gcgcttccaa cgtcattcgc acagcagaat tgtgccatct ctctctttt     1260 tttccccccc tctaaaccgc cacaacggca ccctaagggt taaactatcc aaccagccgc     1320
agcctcagcc tctctcagcc tcatcagcca tggcaccaca cccgacgctc aaggccacct     1380
tcgcggccag gagcgagacg gcgacgcacc cgctgacggc ttacctgttc aagctcatgg     1440
acctcaaggc gtccaacctg tgcctgagcg ccgacgtgcc gacagcgcgc gagctgctgt     1500
acctggccga caagattggc ccgtcgattg tcgtgctcaa gacgcactac gacatggtct     1560
cgggctggga cttccacccg gagacgggca cgggagccca gctggcgtcg ctggcgcgca     1620
agcacggctt cctcatcttc gaggaccgca agtttggcga cattggccac accgtcgagc     1680
tgcagtacac gggcgggtcg gcgcgcatca tcgactgggc gcacattgtc aacgtcaaca     1740
tggtgcccgg caaggcgtcg gtggcctcgc tggcccaggg cgccaagcgc tggctcgagc     1800
gctaccnctg cgaggtcaag acgtccgtca ccgtcggcac gcccaccatg gactcgtttg     1860
acgacgacgc cgactccagg gacgccgagc ccgccgcgc cgtcaacggc atgggctcca     1920
ttggcgtcct ggacaagccc atccactcga accggtccgg cgacggccgc aagggcagca     1980
tcgtctccat caccaccgtc acccagcagt acgagtccgt ctcctcgccc cggttaacaa     2040
aggccatcgc cgagggcgac gagtcgctct tcccgggcat cgaggaggcg ccgctgagcc     2100
gcggcctcct gatcctcgcc caaatgtcca gccaggcaa cttcatgaac aaggagtaca     2160
cgcaggcctg cgtcgaggcc gcccgggagc acaaggactt tgtcatgggc ttcatctcgc     2220
aggagacgct caacaccgag cccgacgatg cctttatcca catgacgccc ggctgccagc     2280
tgccccccga agacgaggac cagcagacca acggatcgg cggtgagac ggccagggcc     2340 agcagtacaa cacgccgcac aagctgattg catcgccgg tagcgacatt gccattgtgg     2400
gccggggcat cctcaaggcc tcagacccccg tagaggaggc agagcggtac cgatcagcag     2460
cgtggaaagc ctacaccgag aggctgctgc gatagggag ggaagggaag aaagaagtaa     2520
```

```
agaaaggcat ttagcaagaa gggggaaaag ggagggagga caaacggagc tgagaaagag    2580
ctcttgtcca aagcccggca tcatagaatg cagctgtatt taggcgacct cttttttccat   2640 cttgtcgatt tttgttatga cgtaccagtt gggatgatgg atgattgtac cccagctgcg    2700
attgatgtgt atcttttgcat gcaacaacac gcgatggcgg aggcgaactg cacattggaa  2760
ggttcatata tggtcctgac atatctggtg gatctggaag catggaattg tattttttgat  2820 ttggcatttg cttttgcgcg tggagggaac atatcaccct cgggcatttt tcatttggta   2880
ggatggtttg gatgcagttg atcgataagc ttgatatcg                          2919
```

<210> SEQ ID NO 8
<211> LENGTH: 20
<212> TYPE: DNA
<213> ORGANISM: Artificial Sequence
<220> FEATURE:
<223> OTHER INFORMATION: synthesized primer

<400> SEQUENCE: 8
ggcttcactt tcgatgtcgt                                                20

<210> SEQ ID NO 9
<211> LENGTH: 20
<212> TYPE: DNA
<213> ORGANISM: Artificial Sequence
<220> FEATURE:
<223> OTHER INFORMATION: synthesized primer

<400> SEQUENCE: 9
gttgaggggg ggtatctttg                                                20

<210> SEQ ID NO 10
<211> LENGTH: 20
<212> TYPE: DNA
<213> ORGANISM: Artificial Sequence
<220> FEATURE:
<223> OTHER INFORMATION: synthesized primer

<400> SEQUENCE: 10
ttgagtcggc gaagagggat                                                20

<210> SEQ ID NO 11
<211> LENGTH: 20
<212> TYPE: DNA
<213> ORGANISM: Artificial Sequence
<220> FEATURE:
<223> OTHER INFORMATION: synthesized primer

<400> SEQUENCE: 11
ctcctccctc tctccctctc                                                20

<210> SEQ ID NO 12
<211> LENGTH: 20
<212> TYPE: DNA
<213> ORGANISM: Artificial Sequence
<220> FEATURE:
<223> OTHER INFORMATION: synthesized primer

<400> SEQUENCE: 12
tcgcatcagg taagctgttg                                                20

<210> SEQ ID NO 13
<211> LENGTH: 20
<212> TYPE: DNA
<213> ORGANISM: Artificial Sequence

```
<220> FEATURE:
<223> OTHER INFORMATION: synthesized primer

<400> SEQUENCE: 13
gcaatcaagc gacggaggac                                               20

<210> SEQ ID NO 14
<211> LENGTH: 20
<212> TYPE: DNA
<213> ORGANISM: Artificial Sequence
<220> FEATURE:
<223> OTHER INFORMATION: synthesized primer

<400> SEQUENCE: 14
agagtgtcgt caccagtata                                               20

<210> SEQ ID NO 15
<211> LENGTH: 20
<212> TYPE: DNA
<213> ORGANISM: Artificial Sequence
<220> FEATURE:
<223> OTHER INFORMATION: synthesized primer

<400> SEQUENCE: 15
gacgggaggg aggatacgta                                               20

<210> SEQ ID NO 16
<211> LENGTH: 20
<212> TYPE: DNA
<213> ORGANISM: Artificial Sequence
<220> FEATURE:
<223> OTHER INFORMATION: synthesized primer

<400> SEQUENCE: 16
aaggagccat ctctactgcg                                               20

<210> SEQ ID NO 17
<211> LENGTH: 20
<212> TYPE: DNA
<213> ORGANISM: Artificial Sequence
<220> FEATURE:
<223> OTHER INFORMATION: synthesized primer

<400> SEQUENCE: 17
tgagagcggt ggtatccacg                                               20

<210> SEQ ID NO 18
<211> LENGTH: 25
<212> TYPE: DNA
<213> ORGANISM: Artificial Sequence
<220> FEATURE:
<223> OTHER INFORMATION: synthesized primer

<400> SEQUENCE: 18
ggtaccacca gacatgacaa tgttg                                         25

<210> SEQ ID NO 19
<211> LENGTH: 20
<212> TYPE: DNA
<213> ORGANISM: Artificial Sequence
<220> FEATURE:
<223> OTHER INFORMATION: synthesized primer

<400> SEQUENCE: 19
acaacgtcct gcagtgtcaa                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: synthesized primer

<400> SEQUENCE: 20
tagcgatctg catcaagggc                                            20

<210> SEQ ID NO 21
<211> LENGTH: 19
<212> TYPE: DNA
<213> ORGANISM: Artificial Sequence
<220> FEATURE:
<223> OTHER INFORMATION: synthesized primer

<400> SEQUENCE: 21
aagaaggtta cccacgccg                                             19

<210> SEQ ID NO 22
<211> LENGTH: 21
<212> TYPE: DNA
<213> ORGANISM: Artificial Sequence
<220> FEATURE:
<223> OTHER INFORMATION: synthesized primer

<400> SEQUENCE: 22
atcaaaggta ccaccaccga g                                          21
```